(12) United States Patent
Yoo et al.

(10) Patent No.: US 11,918,112 B2
(45) Date of Patent: Mar. 5, 2024

(54) SHOE MANAGEMENT APPARATUS

(71) Applicant: LG ELECTRONICS INC., Seoul (KR)

(72) Inventors: Hyunsun Yoo, Seoul (KR); Jeong Guen Choi, Seoul (KR); Joohyeon Oh, Seoul (KR); Jae Myung Lim, Seoul (KR); Byoungjoon Han, Seoul (KR); Sang Yoon Lee, Seoul (KR); Hyunju Kim, Seoul (KR); Jeaseok Seong, Seoul (KR)

(73) Assignee: LG ELECTRONICS INC., Seoul (KR)

(*) Notice: Subject to any disclaimer, the term of this patent is extended or adjusted under 35 U.S.C. 154(b) by 304 days.

(21) Appl. No.: 17/356,200

(22) Filed: Jun. 23, 2021

(65) Prior Publication Data

US 2021/0401168 A1 Dec. 30, 2021

(30) Foreign Application Priority Data

Jun. 24, 2020 (KR) .................. 10-2020-0077410
Jun. 24, 2020 (KR) .................. 10-2020-0077411
Jun. 24, 2020 (KR) .................. 10-2020-0077412
Jun. 24, 2020 (KR) .................. 10-2020-0077413
Jun. 24, 2020 (KR) .................. 10-2020-0077414
Jun. 24, 2020 (KR) .................. 10-2020-0077415
Jun. 24, 2020 (KR) .................. 10-2020-0077417

(Continued)

(51) Int. Cl.
*A47B 61/04* (2006.01)
*A47B 61/00* (2006.01)
(Continued)

(52) U.S. Cl.
CPC ............ *A47B 61/04* (2013.01); *A47B 61/003* (2013.01); *A47L 23/02* (2013.01); *A47L 23/20* (2013.01); *A61L 2/07* (2013.01); *A61L 2/10* (2013.01); *A61L 2/26* (2013.01); *A61L 2202/11* (2013.01); *A61L 2202/122* (2013.01)

(58) Field of Classification Search
CPC ....... A47B 61/04; A47B 61/003; A47L 23/02; A47L 23/20; A61L 2/07; A61L 2/10; A61L 2/26; A61L 2202/11; A61L 2202/122

See application file for complete search history.

(56) References Cited

U.S. PATENT DOCUMENTS 5,509,170 A 4/1996 LoFaro et al.
10,935,305 B1* 3/2021 Bassler ................ F25D 25/024
(Continued)

FOREIGN PATENT DOCUMENTS

EP 2184570 A1 * 5/2010 ............. F25D 25/02
JP 7-24124 A 9/1995
(Continued)

*Primary Examiner* — Matthew W Ing
(74) *Attorney, Agent, or Firm* — Birch, Stewart, Kolasch & Birch, LLP

(57) ABSTRACT

A shoe management apparatus capable of managing various types of shoes and including a cabinet defining an inner space for storing shoes; and a partition dividing the inner space into an upper first compartment and a lower second compartment, formed therein with a fluid path along which air is discharged into the inner space, and variable in length with respect to a front-to-rear direction of the shoe management apparatus.

20 Claims, 10 Drawing Sheets

(30) Foreign Application Priority Data

Dec. 8, 2020 (KR) ........................ 10-2020-0170566
Mar. 9, 2021 (KR) ........................ 10-2021-0031062

(51) Int. Cl.
*A47L 23/02* (2006.01)
*A47L 23/20* (2006.01)
*A61L 2/07* (2006.01)
*A61L 2/10* (2006.01)
*A61L 2/26* (2006.01)

(56) References Cited

U.S. PATENT DOCUMENTS

2012/0042683 A1* 2/2012 Malisi ................... F25D 17/067
          62/426
2012/0091084 A1* 4/2012 Amaral ................ F25D 25/024
          211/80

FOREIGN PATENT DOCUMENTS

| KR | 20-0381792 Y1 | | 4/2005 |
|---|---|---|---|
| KR | 200422381 Y1 | * | 7/2006 |
| KR | 20120004902 U | * | 7/2012 |
| KR | 10-2012-0119542 A | | 10/2012 |
| KR | 10-1410982 B1 | | 6/2014 |

* cited by examiner

[FIG. 1]
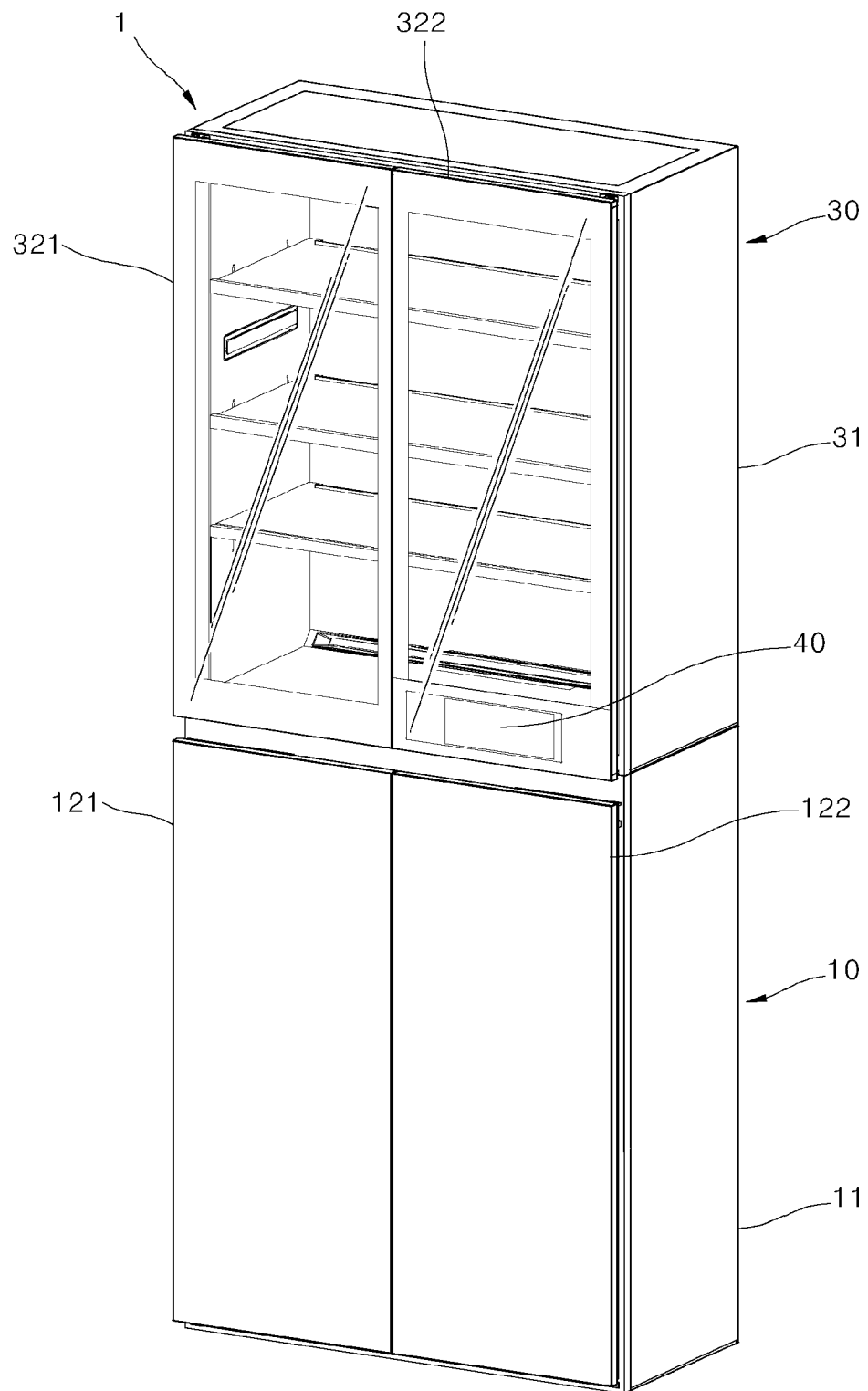

[FIG. 2]
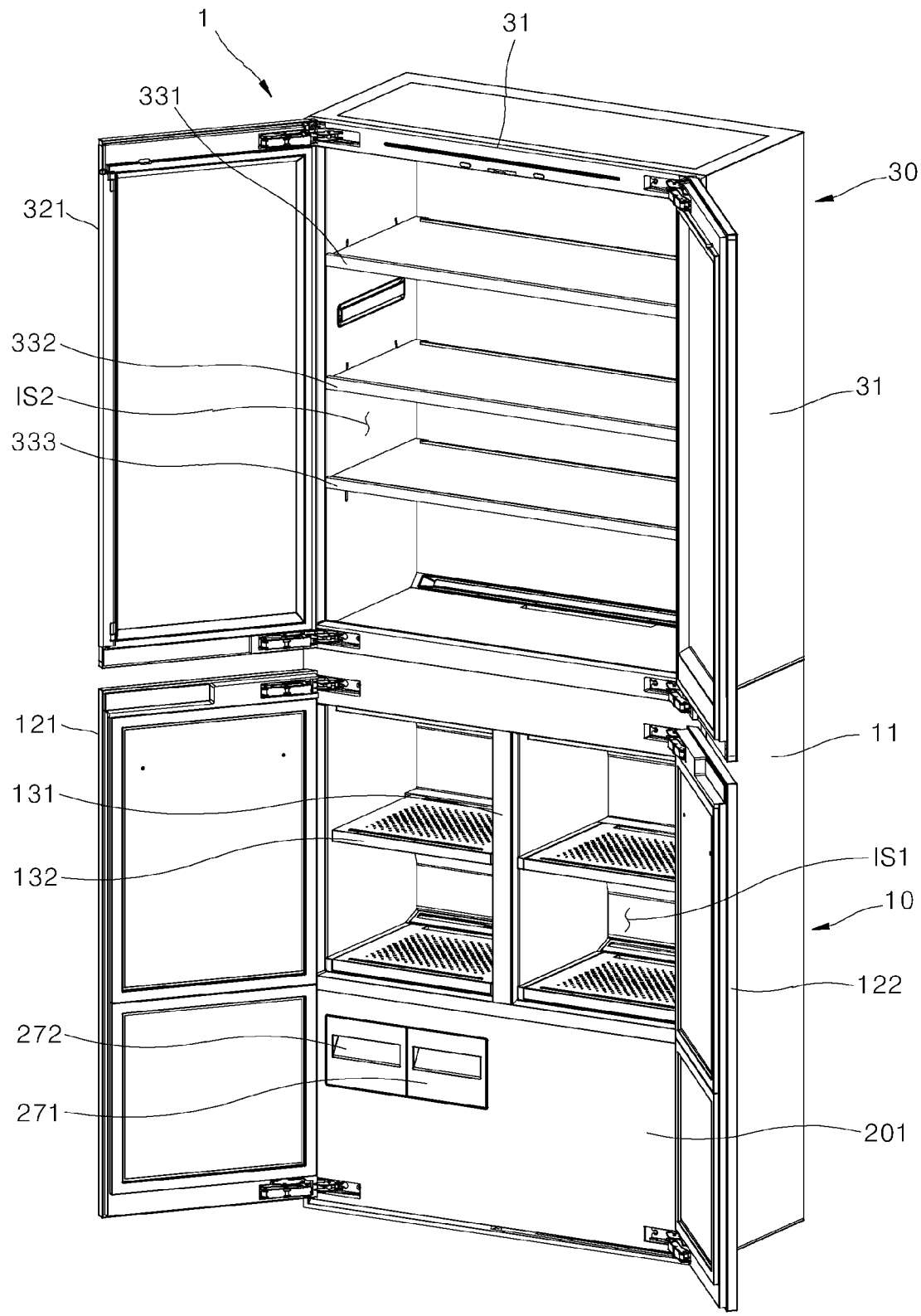

[FIG. 3]
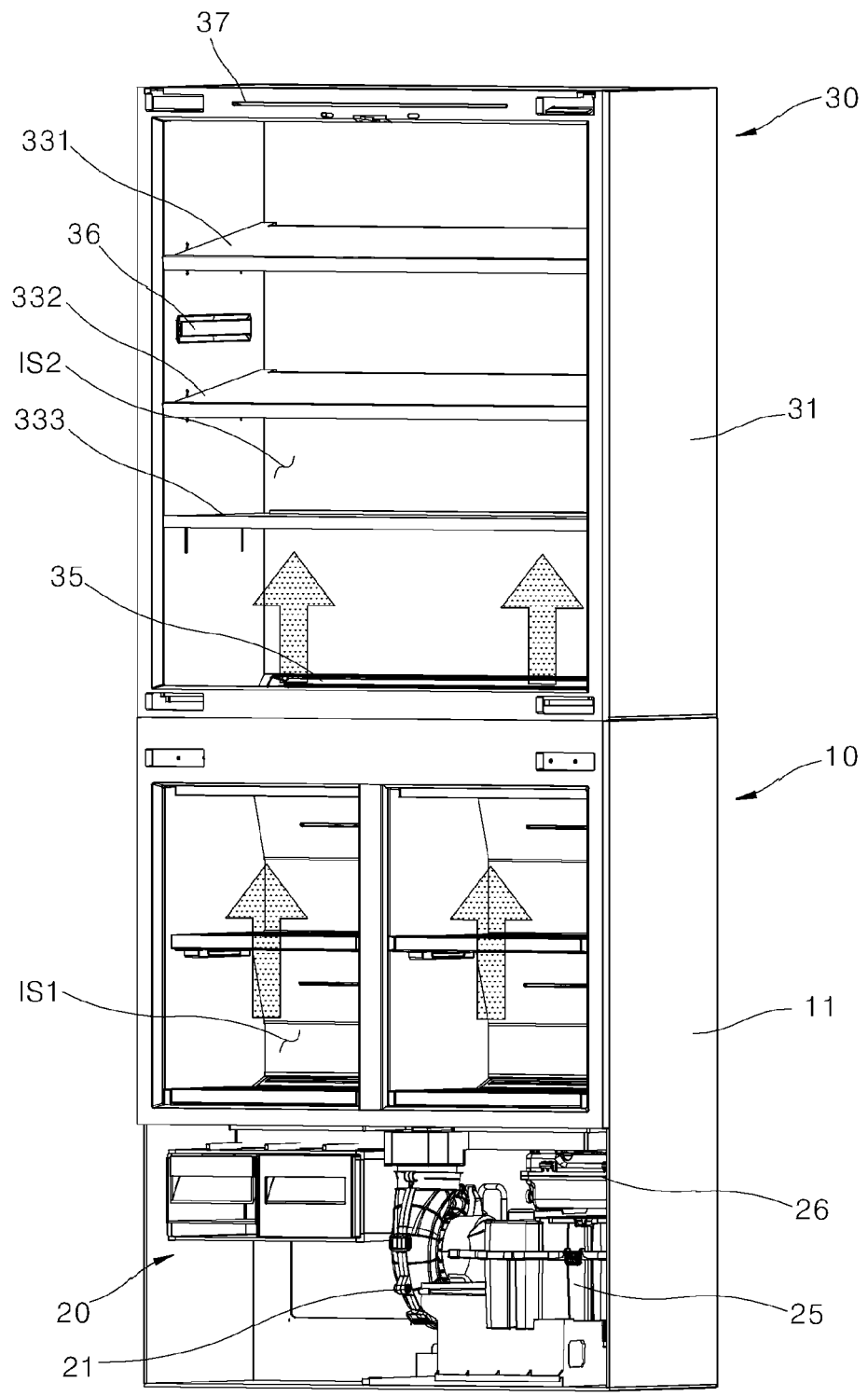

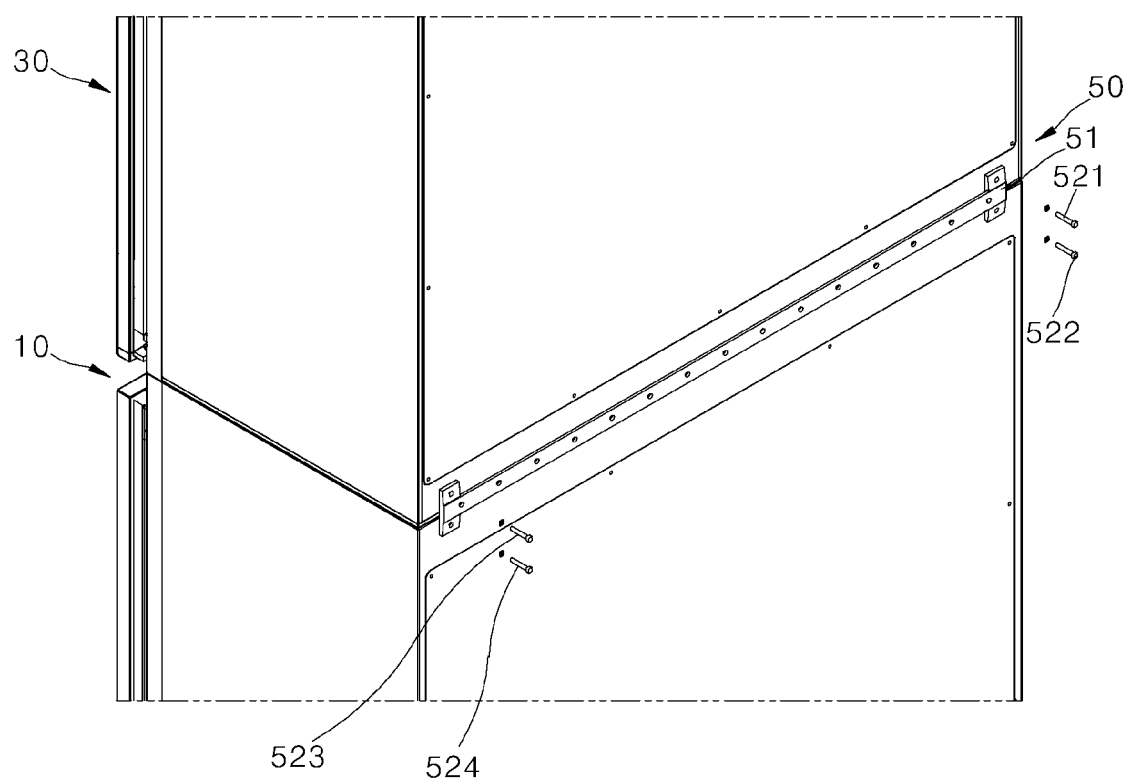
[FIG. 4]

[FIG. 5]
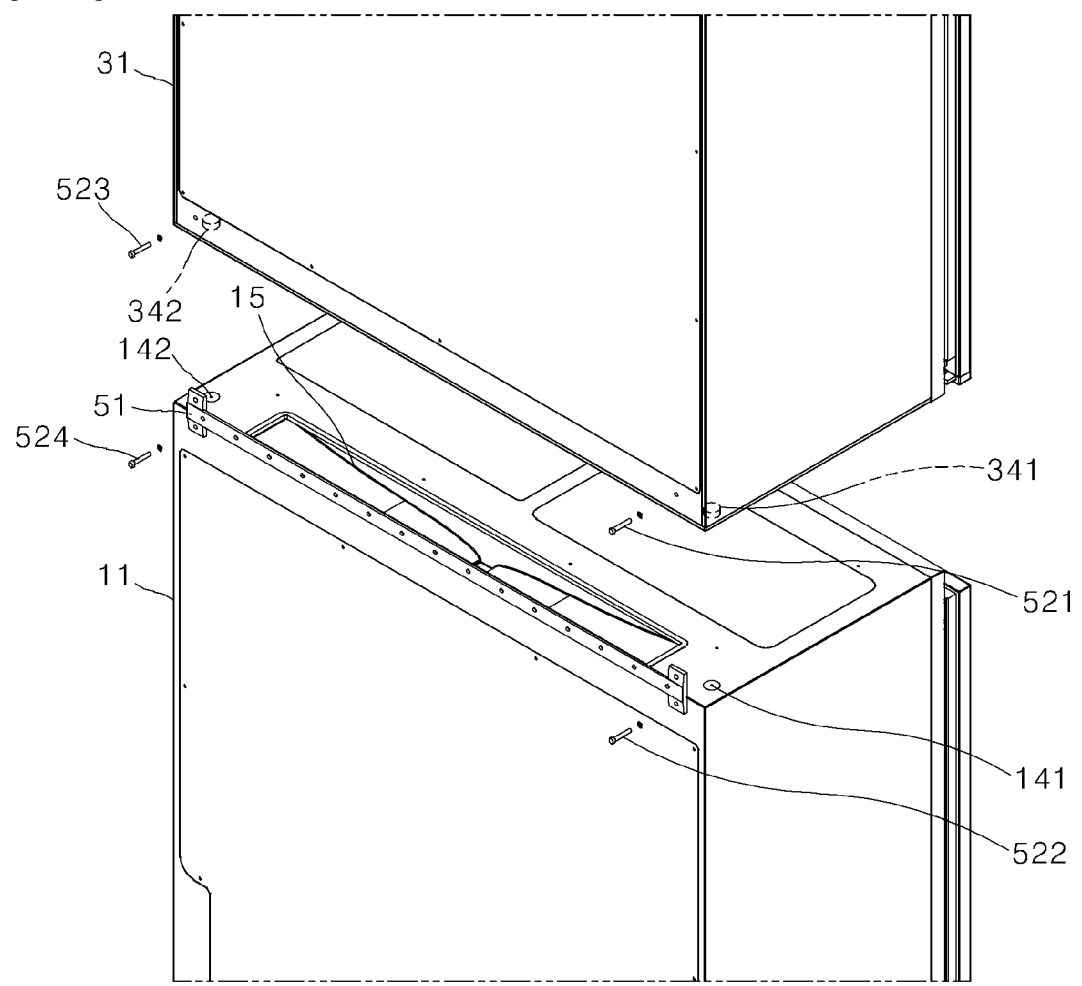

[FIG. 6]
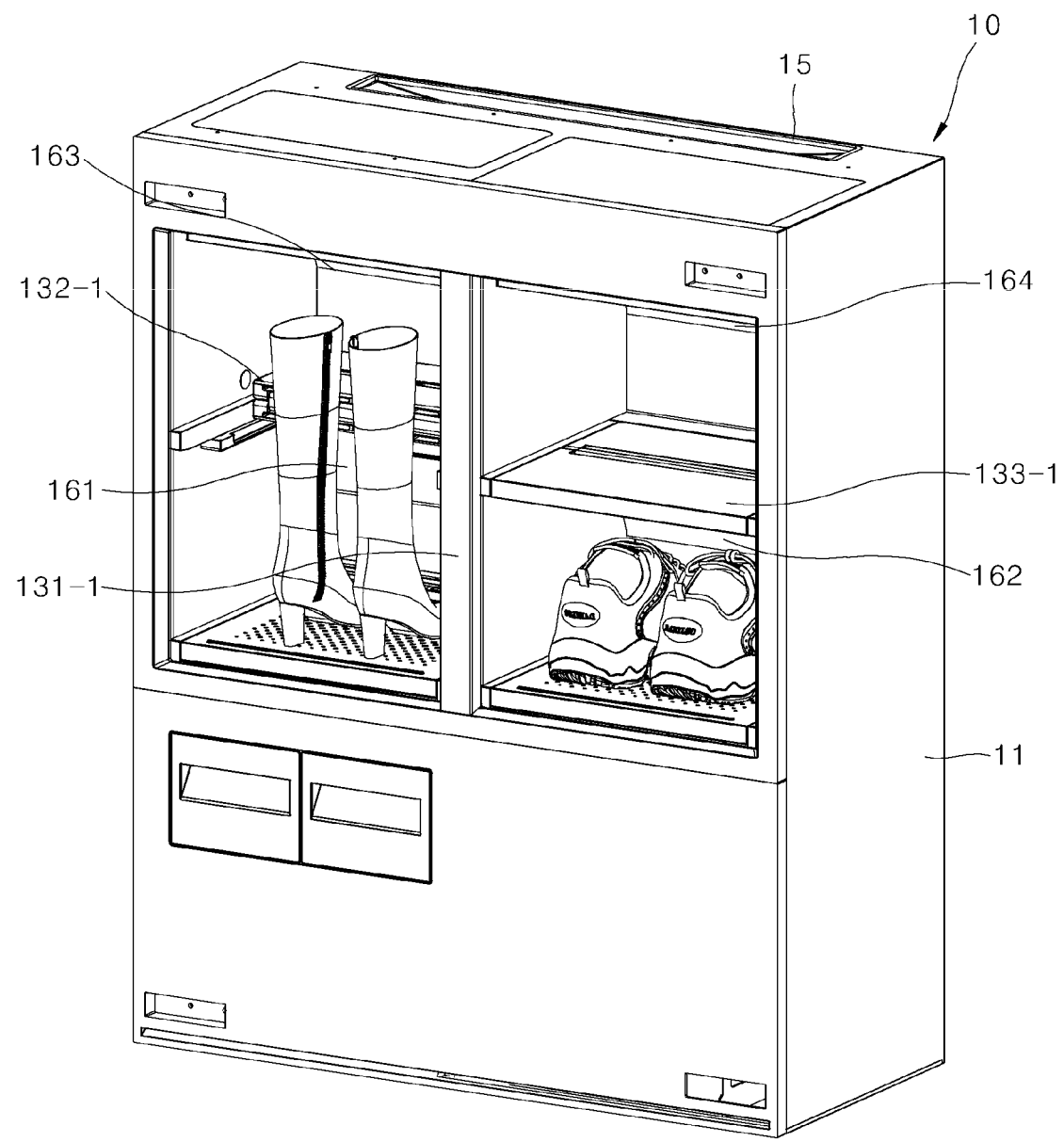

[FIG. 7]
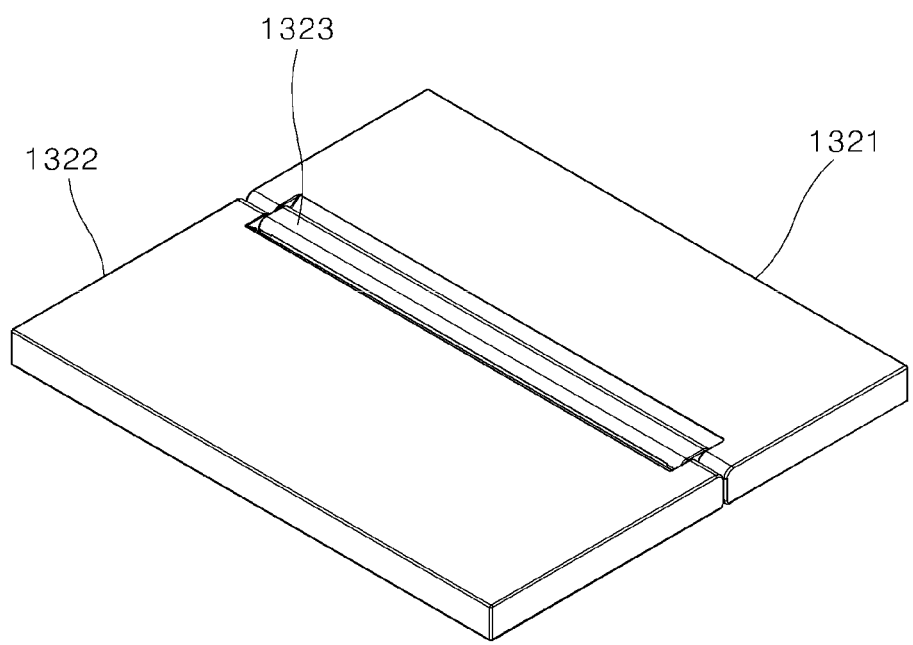

[FIG. 8]
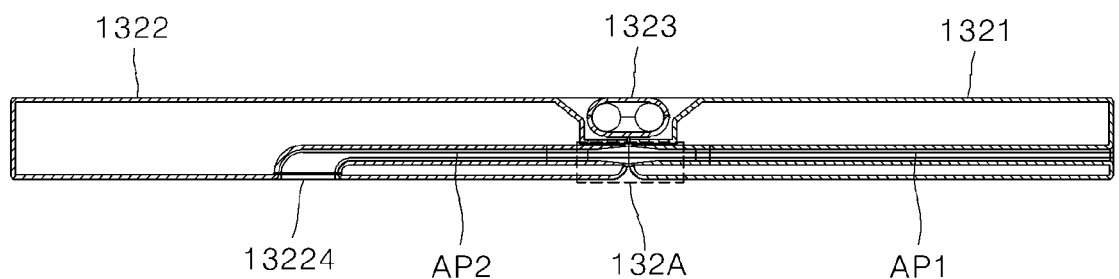
[FIG. 9]
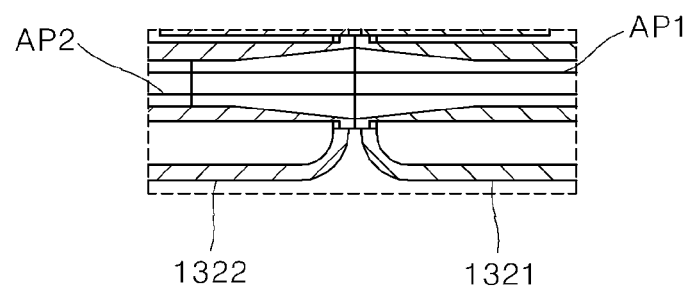

[FIG. 10]
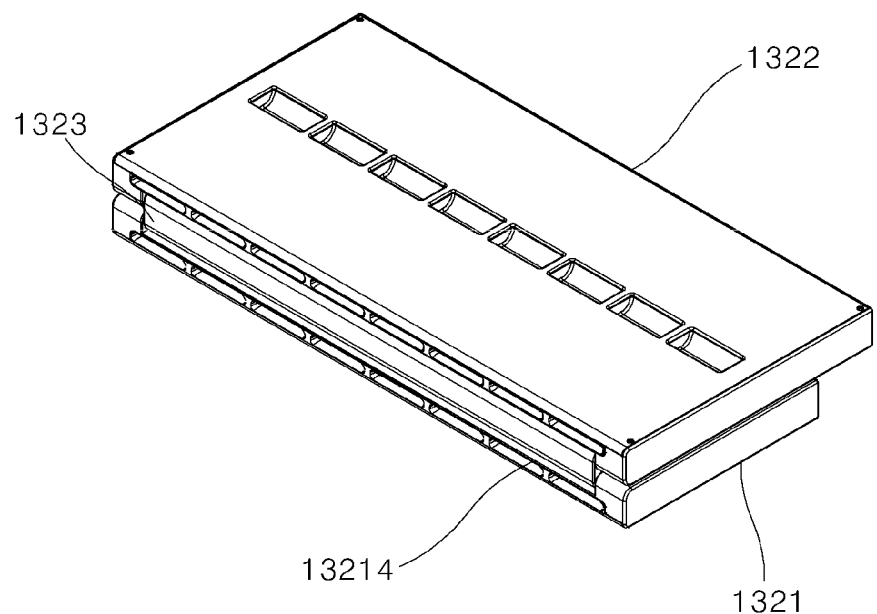
[FIG. 11]
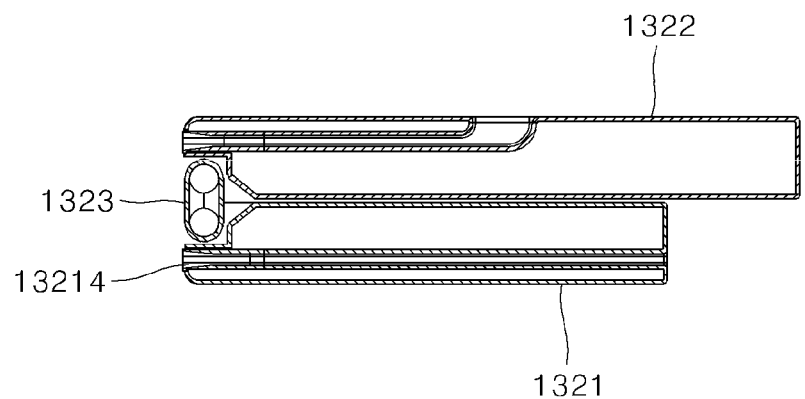

[FIG. 12]
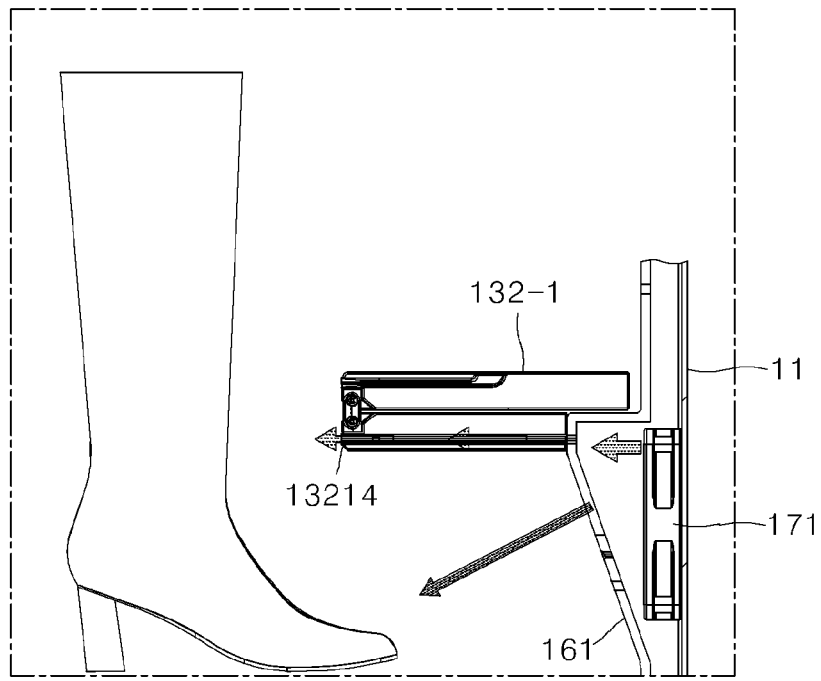
[FIG. 13]
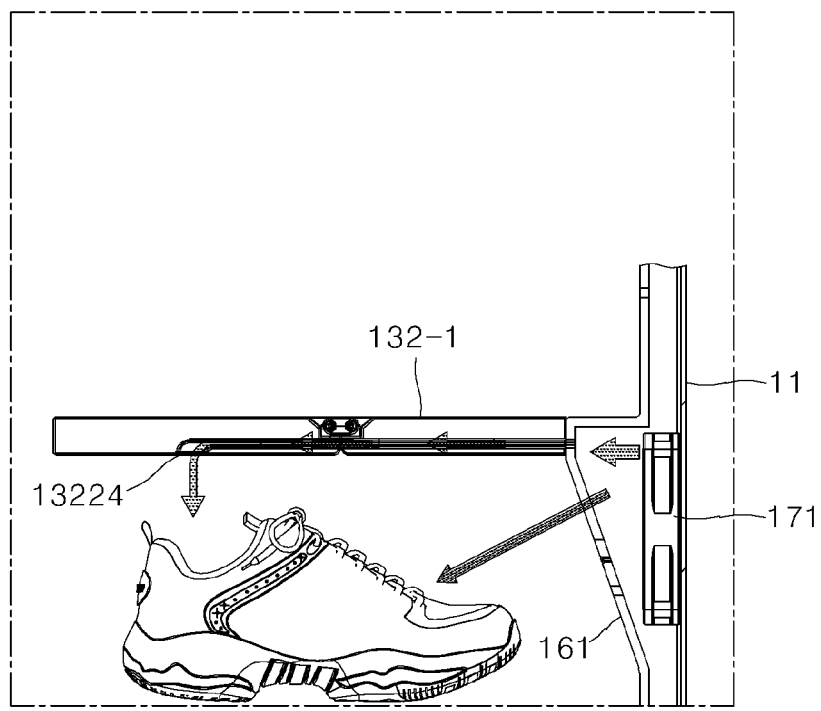

SHOE MANAGEMENT APPARATUS

CROSS-REFERENCE TO RELATED APPLICATIONS

This application claims priority to and the benefit of Korean Patent Application No. 10-2020-0077410, filed on Jun. 24, 2020, Korean Patent Application No. 10-2020-0077411, filed on Jun. 24, 2020, Korean Patent Application No. 10-2020-77412, filed on Jun. 24, 2020, Korean Patent Application No. 10-2020-0077413, filed on Jun. 24, 2020, Korean Patent Application No. 10-2020-77414, filed on Jun. 24, 2020, Korean Patent Application No. 10-2020-0077415, filed on Jun. 24, 2020, Korean Patent Application No. 10-2020-0077417, filed on Jun. 24, 2020, Korean Patent Application No. 10-2020-0170566, filed on Dec. 8, 2020, and Korean Patent Application No. 10-2021-0031062, filed on Mar. 9, 2021, the disclosures of which are incorporated herein by reference in their entirety into the present application.

BACKGROUND OF THE INVENTION

1. Field of the Invention

The present disclosure relates to a shoe management apparatus that can perform at least one function selected from among storage, sterilization, and decontamination of shoes.

2. Description of the Background Art

Generally, a shoe rack installed in an entrance room of a building is used to hold and organize various types of shoes.

However, when shoes wet with water or sweat are stored in a shoe rack, the humidity inside the shoe rack increases, causing deterioration and reduction in lifespan of all shoes stored therein. In particular, with increasing demand for high-end shoes in recent years, interest is growing in an apparatus that can properly manage shoes to extend lifespan of the shoes.

In addition, shoes are generally used for outdoor activities and thus can be easily contaminated with dust, bacteria, and viruses. Therefore, it is important from the viewpoint of hygiene for households to frequently perform sterilization or decontamination of shoes.

SUMMARY OF THE INVENTION

Embodiments of the present disclosure provide a shoe management apparatus that can more effectively perform sterilization and/or dust removal for various types of shoes.

Embodiments of the present disclosure provide a shoe management apparatus that is variable in air exhaust location and/or air exhaust direction depending on the types of shoes.

Embodiments of the present disclosure provide a shoe management apparatus that can more effectively discharge air to shoes.

The above and other objects and advantages of the present disclosure will become apparent from the detailed description of the following embodiments in conjunction with the accompanying drawings. In addition, it will be readily understood that the objects and advantages of the present disclosure can be realized by features set forth in the appended claims or combinations thereof.

In accordance with one aspect of the present disclosure, a shoe management apparatus includes a partition disposed in an inner space for storing shoes and variable in air exhaust location and air exhaust direction therethrough.

In accordance with another aspect of the present disclosure, a shoe management apparatus includes a partition dividing an inner space for storing shoes into two compartments from top to bottom and variable in length with respect to a front-to-rear direction of the shoe management apparatus.

In accordance with a further aspect of the present disclosure, a shoe management apparatus includes: a cabinet defining an inner space for storing shoes; and a partition disposed in the inner space and having a first position in which air is discharged through the partition in a downward direction from a front region of the inner space with reference to a front-to-rear direction of the shoe management apparatus and a second position in which air is discharged through the partition in a forward direction from a middle region of the inner space with reference to the front-to-rear direction.

In an embodiment, the partition may include a first plate, a plate connection portion, and a second plate. The first plate may be coupled to the cabinet at a rear portion of the inner space and may be formed on a front surface thereof with a first plate exhaust port through which air is discharged. The plate connection portion may be pivotally coupled to the first plate. The second plate may be pivotally coupled to the plate connection portion and may be formed on a lower surface thereof with a second plate exhaust port through which air is discharged.

In an embodiment, the plate connection part may be pivotally coupled to a front upper portion of the first plate and a rear upper portion of the second plate.

In an embodiment, when the partition is in the first position, the second plate may be located in front of the first plate and, when the partition is in the second position, the second plate may be located on an upper surface of the first plate.

In an embodiment, the shoe management apparatus may further include: an inner panel disposed at a rear upper portion of a region under the partition in the inner space with an upper end of the inner panel located ahead of a lower end of the inner panel. In addition, the shoe management apparatus may further include: a blower fan disposed between the inner panel and an inner surface of the cabinet to force air to a plate fluid path formed inside the partition.

In an embodiment, the inner panel may be formed with an inner panel exhaust port through which air is discharged in an obliquely downward direction.

In an embodiment, the shoe management apparatus may further include: an electric compartment disposed under the inner space and discharging air into the inner space.

In accordance with yet another aspect of the present disclosure, a shoe management apparatus includes: a cabinet defining an inner space for storing shoes; and a partition dividing the inner space into an upper first compartment and a lower second compartment, formed therein with a fluid path along which air is discharged into the inner space, and variable in length with respect to a front-to-rear direction of the shoe management apparatus.

In an embodiment, the partition may have a first length and a second length with respect to the front-to-rear direction, the first length allowing air to be discharged in a downward direction from the partition, the second length allowing air to be discharged in a forward direction from the partition.

In an embodiment, the partition may include a first plate, a plate connection portion, and a second plate.

When the second plate is located in front of the first plate, the partition may have the first length with respect to the front-to-rear direction.

In addition, when the second plate is located on an upper surface of the first plate, the partition may have the second length with respect to the front-to-rear direction.

The shoe management apparatus according to the present disclosure can more effectively perform various management operations for various types of shoes.

The shoe management apparatus according to the present disclosure can appropriately adjust air exhaust direction and air exhaust location depending on the types of shoes.

The shoe management apparatus according to the present disclosure can more effectively discharge air to shoes.

The above and other effects of the present disclosure will become apparent from the following detailed description of the present disclosure.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 is a perspective view of a shoe management apparatus according to an embodiment of the present disclosure.

FIG. 2 is a front view of the shoe management apparatus according to the embodiment of the present disclosure shown in FIG. 1, with doors opened.

FIG. 3 is a perspective view of the shoe management apparatus according to the embodiment of the present disclosure shown in FIG. 1, with the doors and an electric compartment front panel removed therefrom.

FIG. 4 is a partial view of a back surface of the shoe management apparatus according to the embodiment of the present disclosure shown in FIG. 1.

FIG. 5 is a partial view of the shoe management apparatus according to the embodiment of the present disclosure shown in FIG. 1, with a first management apparatus separated from a second management apparatus.

FIG. 6 is a perspective view of the first management apparatus of the shoe management apparatus according to the embodiment of the present disclosure shown in FIG. 1, with the doors removed therefrom.

FIG. 7 is a perspective view of a 2nd first partition of the shoe management apparatus according to an embodiment of the present disclosure, wherein the 2nd first partition is in an unfolded position.

FIG. 8 is a sectional view of a 2nd first partition of the shoe management apparatus according to the embodiment of the present disclosure, wherein the 2nd first partition is in the unfolded position.

FIG. 9 is an enlarged view of section 132A of FIG. 8.

FIG. 10 is a perspective view of the 2nd first partition of the shoe management apparatus according to the embodiment of the present disclosure, wherein the 2nd first partition is in a folded position.

FIG. 11 is a sectional view of the 2nd first partition of the shoe management apparatus according to the embodiment of the present disclosure, wherein the 2nd first partition is in the folded position.

FIG. 12 shows a case in which a boot is placed in the first management apparatus of the shoe management apparatus according to the embodiment of the present disclosure.

FIG. 13 shows a case in which a sneaker is placed in the first management apparatus of the shoe management apparatus according to the embodiment of the present disclosure.

DETAILED DESCRIPTION

Reference will now be made in detail to various embodiments, examples of which are illustrated in the accompanying drawings such that the present disclosure can be easily implemented by those skilled in the art. Description of known functions and constructions which may unnecessarily obscure the subject matter of the present disclosure will be omitted. Like components will be denoted by like reference numerals throughout the specification.

It will be understood that, although the terms "first," "second," and the like may be used herein to describe various elements and the like, these elements should not be limited by these terms. These terms are only used to distinguish one element from another element. Thus, a first element discussed below could be termed a second element, or vice versa, without departing from the scope of the present disclosure.

It will be understood that when a component is referred to as being disposed "at an upper (lower) portion of" or "on" (or "under") another component, it can be directly formed to adjoin an upper surface ("a lower surface") of the other component, or intervening component(s) may also be interposed therebetween.

In addition, when a certain component is referred to as being "connected to", "coupled to" or "joined to" another component, these components may be directly connected to, coupled to or joined to each other or through another component, or intervening component(s) may also be "interposed" therebetween.

As used herein, the singular forms, "a," "an," and "the" are intended to include the plural forms as well, unless the context clearly indicates otherwise. Moreover, the terms "comprises," "comprising," "includes," and/or "including," when used in this specification, should not be construed to mean that a process, method, article, or apparatus comprising a list of elements or steps necessarily comprises all the elements or all the steps. Thus, such a process, method, article, or apparatus may be free from some of the elements or the steps, or may further include one or more other elements or steps.

Hereinafter, a shoe management apparatus according to some exemplary embodiments of the present disclosure will be described.

FIG. 1 is a perspective view of a shoe management apparatus 1 according to an embodiment of the present disclosure. The shoe management apparatus 1 may include a first management apparatus 10 and a second management apparatus 30. The first management apparatus 10 may include a first cabinet 11, a 1st first door 121, and a 2nd first door 122, and the second management apparatus 30 may include a second cabinet 31, a 1st second door 321, and a 2nd second door 322. The shoe management apparatus 1 may further include a display unit 40. The display unit 40 may be an electronic visual display, such as an LCD, TFT-LCD, OLED, a flexible display, and a three-dimensional display.

The first management apparatus 10 may be disposed at a lower portion of the shoe management apparatus 1. The first management apparatus 10 may perform at least one operation selected from among removal of contaminants, such as dust, sterilization, deodorization, dehumidification, drying, and coating for shoes placed therein. Here, the sterilization operation may include at least one selected from among ultraviolet (UV) sterilization and steam sterilization. UV sterilization may be an operation of irradiating the shoes with short-wave UV rays having a wavelength of about 100 nm to 280 nm. Steam sterilization may be an operation of sterilizing the shoes using steam generated by heating water. The steam may be generated by heating water to 100° C. In addition, the generated steam may have a temperature of 40° C. to 50° C.

The first management apparatus 10 may be an apparatus that performs at least two of the aforementioned operations (that is, contaminant removal, sterilization, deodorization, dehumidification, drying, and coating) for a relatively short period of time in order to remove contamination of shoes placed therein. For example, the first management apparatus may sequentially perform removal of contaminants, such as dust, from surfaces of the shoes placed therein, sterilization and deodorization using the short-wave UV rays and a photocatalyst, sterilization using steam, dehumidification and drying, and coating for providing repellency to water for a predetermined period of time (for example, 40 minutes). That is, the first management apparatus 10 may be referred to as an "intensive care apparatus".

The first cabinet 11 of the first management apparatus 10 may define an exterior of the first management apparatus 10. The first cabinet 11 may be provided in the form of a cuboid open at a front thereof.

The 1st first door 121 and the 2nd first door 122 of the first management apparatus 10 may be disposed at the front of the first cabinet 11.

The second management apparatus 30 may be disposed on an upper surface of the first management apparatus 10. The second management apparatus 30 may perform at least one operation selected from among sterilization, ventilation, and humidity control of a space in which shoes are placed. Here, the sterilization operation may be performed using the short-wave ultraviolet rays described above or a photocatalytic filter.

The second management apparatus 30 may be an apparatus that constantly performs operations necessary for preventing deterioration of shoes stored therein. That is, the second management apparatus 30 may be referred to as a "constant management apparatus" or "light care apparatus".

The second cabinet 31 of the second management apparatus 30 may define an exterior of the second management apparatus 30. The second cabinet 31 may be provided in the form of a cuboid open at a front thereof.

The 1st second door 321 (that is, a first upper door) and the 2nd second door 322 of the second management apparatus may be disposed at the front of the second cabinet 31.

The display unit 40 may display a current operating state, abnormality, or the like of the shoe management apparatus 1. The display unit 40 may be disposed at a lower portion of the 2nd second door 322.

For convenience of description, a side or portion of the shoe management apparatus 1 at which the doors 121, 122, 321, 322 are disposed is defined as "front" and the other side or portion of the shoe management apparatus 1 is defined as "rear".

FIG. 2 is a front view of the shoe management apparatus 1 according to the embodiment of the present disclosure shown in FIG. 1, with the doors opened.

The first management apparatus 10 may be formed at an upper portion thereof with a first inner space IS1 for storing shoes and may include an electric compartment disposed under the first inner space IS1. An electric compartment front panel 201 may be disposed at a front of a space for the electric compartment. That is, the first cabinet 11 may define the first inner space IS1 and the space for the electric compartment, and the front of the electric compartment may be covered by the electric compartment front panel 201.

The space for the electric compartment may contain devices for dehumidifying air in the electric compartment, devices for discharging the dehumidified air to the first inner space IS1 and a second inner space IS2, a water supply container 271, and a drain container 272. The water supply container 271 may be detachably coupled to the first cabinet 11. The water supply container 271 may supply water to a steam generator 26 of the electric compartment 20.

The first management apparatus 10 may include at least one first partition dividing the first inner space IS1 into multiple compartments. The first partition may include a partition dividing the first inner space IS1 from side to side.

As in this embodiment, the first inner space IS1 may be divided by a 1st first partition 131, a 2nd first partition 132, and a 3rd first partition 133. The 1st first partition 131 may divide the first inner space IS1 from side to side. The 1st first partition 131 may be disposed at a center of the first inner space IS1 with reference to the side-to-side direction. Each of the 2nd first partition 132 and the 3rd first partition 133 may divide the first inner space IS1 from top to bottom.

The second management apparatus 30 may be formed with a second inner space IS2 for storing shoes. That is, the second cabinet 31 may define the second inner space IS2 for storing shoes.

The second management apparatus 30 may include at least one second partition dividing the second inner space IS2 into multiple compartments. The second partition may include at least one partition dividing the second inner space IS2 from top to bottom.

As in this embodiment, the second inner space IS2 may be divided from top to bottom by a 1st second partition 331, a 2nd second partition 332, and a 3rd second partition 333.

FIG. 3 is a perspective view of the shoe management apparatus 1 according to the embodiment of the present disclosure shown in FIG. 1, with the doors 121, 122, 321, 322 and the electric compartment front panel 201 removed therefrom. In FIG. 3, arrows indicate air flow directions.

As described above, the electric compartment 20 is disposed at a lower portion of the first management apparatus 10. The electric compartment 20 may be formed separately from the first management apparatus 10 or may be formed integrally with the first management apparatus 10. Herein, the present disclosure will be described with reference to an example in which the electric compartment 20 is formed integrally with the first management apparatus 10.

The electric compartment 20 may force a fluid to flow in or out of the electric compartment. That is, the electric compartment 20 may supply the fluid to the first inner space IS1 and/or the second inner space IS2. Alternatively, the electric compartment 20 may draw in the fluid from the first inner space IS1 and/or the second inner space IS2. Here, the fluid may be air, steam, or a material containing substances necessary for management of shoes.

The electric compartment 20 draws in air, dehumidifies the drawn-in air, and discharges the dehumidified air. The electric compartment 20 may include a main fan 21 that draws in air, dehumidifies the drawn-in air, and discharges the dehumidified air. The electric compartment 20 may further include a housing 25 and a steam generator 26 that generates steam by heating water. The steam generator 26 may heat water to 100° C. The housing 25 may define a space for drying and/or heating air. The housing 25 may be formed on an upper surface thereof with an opening 251 through which air is introduced into the housing, may be formed therein with a space for accommodating a heat pump (more specifically, a condenser and/or an evaporator of the heat pump), and may be formed on a side surface thereof with an opening connected to the main fan 21 (specifically, a housing 25 of the main fan).

The air discharged from the electric compartment 20 may be delivered to the first inner space IS1 of the first management apparatus 10 and/or the second inner space IS2 of the second management apparatus 30. To this end, the shoe management apparatus may be formed with a first fluid path communicating between a main fan in the electric compartment 20 and the first inner space IS1 and a second fluid path communicating between the main fan in the electric compartment 20 and the second inner space IS2.

The air inside the first inner space IS1 may be drawn back into the electric compartment. To this end, the shoe management apparatus may be formed with a return fluid path extending through the first inner space IS1 and the electric compartment 20.

The second management apparatus 30 may include a second exhaust port 35 through which the air delivered from the electric compartment 20 is discharged to the second inner space IS2. The second exhaust port 35 may be disposed at a rear bottom of the second inner space IS2 defined by the second cabinet 31, but the second exhaust port 35 may be disposed on any portion of a bottom surface of the second inner space IS2.

In addition, the second management apparatus 30 may include a circulation filter 36 removing harmful substances from the air inside the second inner space IS2. The circulation filter 36 may be disposed on an inner side surface of the second cabinet 31. Although one circulation filter 36 is shown in FIG. 3, it will be understood that the present disclosure is not limited thereto and the second management apparatus 30 may include multiple circulation filters 36. For example, another circulation filter may be disposed opposite the circulation filter 36 in FIG. 3.

In addition, the second management apparatus 30 may include a front discharge port 37 through which air in the second inner space IS2 is discharged to an outside of the shoe management apparatus. The front discharge port 37 may be disposed on an upper front surface of the second cabinet 31.

In addition, at least one of the partitions 331, 332, 333 of the second management apparatus 30 may be variable in angle with respect to a front-to-rear direction of the shoe management apparatus. That is, at least one of the partitions 331, 332, 333 of the second management apparatus 30 may be movable so as to be positioned at various different angles. When the multiple partitions are configured to be variable in angle with respect to the front-to-rear direction, each of the multiple partitions may be independently variable in angle with respect to the front-to-rear direction. With the configuration in which at least one of the partitions 331, 332, 333 is variable in angle with respect to the front-to-rear direction, the air in the second inner space IS2 can flow in various forms, thereby securing uniform ventilation throughout the second inner space IS2, including corners thereof.

As shown in FIG. 1, FIG. 2 and FIG. 3, the shoe management apparatus 1 according to the embodiment of the present disclosure may include: the first management apparatus including the electric compartment 20 and formed with the first inner space IS1 for storing shoes; and the second management apparatus 30 disposed on the upper surface of the first management apparatus 10 and formed with the second inner space IS2 for storing shoes. The electric compartment 20 may be disposed at the lower portion of the first management apparatus 10, and the first inner space IS1 may be formed on an upper side of the space for the electric compartment 20. The first management apparatus 10 may perform at least one operation selected from among contaminant removal, sterilization, deodorization, dehumidification, drying, and coating for shoes placed in the first inner space IS1 with relatively high intensity for a relatively short period of time (or any intensity level for any amount of time), and the second management apparatus 30 may perform at least one operation selected from among sterilization, ventilation, and dehumidification of the second inner space IS2 with relatively low intensity for a relatively long period of time (or with any intensity level for any amount of time), the intensity of the at least one operation of the second management apparatus 30 is less than the intensity of the at least one operation of the first management apparatus 10.

Here, "relatively high intensity" means that the temperature of the steam used in the sterilization operation is relatively high, the intensity of the UV rays used in the sterilization operation is relatively high, or the intensity of the airflow applied to shoes is relatively high.

As such, the shoe management apparatus according to this embodiment of the present disclosure can quickly remove contamination of shoes while allowing long-term storage of shoes without deterioration of the shoes. In addition, the shoe management apparatus according to this embodiment of the present disclosure can be built-in in an entrance room of a building due to structural compactness thereof.

In addition, according to this embodiment of the present disclosure, dehumidified air can be supplied to two management apparatuses using one electric compartment. Thus, it is possible to reduce the overall size of the shoe management apparatus.

FIG. 4 is a partial view of a back surface of the shoe management apparatus according to the embodiment of the present disclosure shown in FIG. 1. Referring to FIG. 4, the shoe management apparatus may include a longitudinal fastener 50 coupling the first management apparatus 10 to the second management apparatus 30. The longitudinal fastener 50 may include a longitudinal connection bar 51 and multiple longitudinal connection screws 521, 522, 523, 524.

Referring to FIG. 4, the shoe management apparatus according to the embodiment of the present disclosure may have a structure in which the first management apparatus 10 and the second management apparatus 30 are stacked vertically (i.e., in a vertical direction).

The longitudinal fastener 50 may couple the stacked first management apparatus 10 and second management apparatus 30 to each other. The longitudinal fastener 50 may be disposed on the back surface (i.e., rear surface) of the shoe management apparatus 1.

The longitudinal connection bar 51 may be disposed at a joint between the first management apparatus 10 and the second management apparatus 30 to be partially located on a back surface (i.e., rear surface) of the first management apparatus 10 and partially located on a back surface (i.e., rear surface) of the second management apparatus 30. The longitudinal connection bar 51 may have a horizontally elongated "H" shape, as viewed from behind the shoe management apparatus.

The longitudinal connection screws 521, 522, 523, 524 serve to securely couple the connection bar 51 to the first management apparatus 10 or the second management apparatus 30. Specifically, the longitudinal connection screws 521, 523 may couple the longitudinal connection bar 51 to the second management apparatus 30, and the longitudinal connection screws 522, 524 may couple the longitudinal connection bar 51 to the first management apparatus 10. When viewed from behind the shoe management apparatus, the longitudinal connection screws 521, 522 may be disposed on the right and the connection screws 523, 524 may be disposed on the left.

FIG. 5 is a partial view of the shoe management apparatus 1 according to the embodiment of the present disclosure shown in FIG. 1, with the first management apparatus 10 separated from the second management apparatus 30.

The first cabinet 11 of the first management apparatus 10 may include first signal contacts 141, 142 disposed on the upper surface thereof. In addition, the second cabinet 31 of the second management apparatus 30 may include second signal contacts 341, 342 disposed on the lower surface thereof.

Upon stacking the second management apparatus 30 on the upper surface of the first management apparatus 10, the first signal contacts 141, 142 may contact the second signal contacts 341, 342, respectively. The first management apparatus 10 may exchange necessary signals (data) with the second management apparatus 30 through signal transmission via the first signal contacts 141, 142 and the second signal contacts 341, 342. The signal transmission may be a wireless transmission, such as Bluetooth™, Zigbee™, Wi-Fi, etc.

In addition, the first management apparatus 10 may include a first exhaust port 15 disposed at an upper end thereof (i.e., the upper surface). Upon stacking the second management apparatus 30 on the upper surface of the first management apparatus 10, the first exhaust port 15 may be connected to the second exhaust port 35 of the second management apparatus 30. In this way, the air delivered from the electric compartment 20 can be discharged into the second inner space IS2 through the first exhaust port 15 of the first management apparatus 10 and through the second exhaust port 35 of the second management apparatus 30.

In an embodiment, the first management apparatus 10 may be used alone in the shoe management apparatus 1, unlike in the embodiments shown in FIG. 1 to FIG. 5. In this embodiment, the first exhaust port 15 may be used to dehumidify a space in which the shoe management apparatus 1 is installed (for example, an entrance room of a building).

FIG. 6 is a perspective view of the first management apparatus 10 of the shoe management apparatus 1 according to the embodiment of the present disclosure shown in FIG. 1, with the doors 121, 122 removed therefrom.

The first management apparatus 10 may include multiple partitions 131-1, 132-1, 133-1 and multiple inner panels 161, 162, 163, 164. Although not shown, the first management apparatus 10 may further include multiple blower fans disposed at the rear of the multiple inner panels 161, 162, 163, 164, respectively.

In terms of arrangement and function, the 1st first partition 131-1, the 2nd first partition 132-1, and the 3rd first partition 133-1 may be substantially the same as the 1st first partition 131, the 2nd first partition 132, and the 3rd first partition 133 described above with reference to FIG. 2, respectively.

However, according to this embodiment, the 2nd first partition 132-1 and/or the 3rd first partition 133-1 may be variable in length with reference to the front-to-rear direction. For example, as shown in FIG. 12, the 2nd first partition 132-1 and/or the 3rd first partition 133-1 may be folded such that one portion of the partition 132-1 and/or the partition 133-1 lies on an upper surface of the other portion thereof to have a relatively short length with reference to the front-to-rear direction. Alternatively, the 2nd first partition 132-1 and/or the 3rd first partition 133-1 may be unfolded to have a relatively long length with reference to the front-to-rear direction.

In addition, according to this embodiment, the 2nd first partition 132-1 and/or the 3rd first partition 133-1 may be variable in direction and location where air is discharged therethrough. For example, the 2nd first partition 132-1 and/or the 3rd first partition 133-1 may be switched between a position in which air is discharged therethrough in a downward direction from a front region of the first inner space IS1 of the first management apparatus 10 with reference to the front-rear direction and a position in which air is discharged therethrough in a forward direction from a middle region of the first inner space IS1 of the first management apparatus 10 with reference to the front-to-rear direction.

Herein, the front region of the first inner space IS1 with reference to the front-rear direction refers to a front section among three sections formed by virtually dividing the first inner space IS1 from front to rear. In addition, the middle region of the first inner space IS1 with reference to the front-rear direction refers to a middle section among the three sections formed by virtually dividing the first inner space IS1 from front to rear. Further, a rear region of the first inner space IS1 with reference to the front-rear direction refers to a rear section among the three sections formed by virtually dividing the first inner space IS1 from front to rear.

The multiple inner panels 161, 162, 163, 164 may be disposed at rear upper portions of the compartments partitioned off by the partitions 131-1, 132-1, 133-1, respectively. In addition, an air flow path and a space for accommodating the blower fan may be defined between the first cabinet 11 and each of the multiple inner panels 161, 162, 163, 164. Further, each of the multiple inner panels 161, 162, 163, 164 may be disposed at an acute angle to the inner surface of the first cabinet 11. That is, each of the multiple inner panels 161, 162, 163, 164 may be disposed with an upper end thereof located ahead of a lower end thereof.

In addition, each of the multiple inner panels 161, 162, 163, 164 may be formed with an inner panel exhaust port. That is, each of the multiple inner panels 161, 162, 163, 164 allows air to be discharged therethrough in an obliquely downward direction from the rear of the first inner space IS1 (more specifically, the rear region of each corresponding compartment) with reference to the front-rear direction. The air exhaust direction may be adjusted by changing a relative position of the inner panel exhaust port with respect to the blower fan at the rear of each of the inner panels 161, 162, 163, 164.

FIG. 7 is a perspective view of the 2nd first partition 132-1 of the shoe management apparatus according to an embodiment of the present disclosure, wherein the 2nd first partition is in an unfolded position. Referring to FIG. 7, the 2nd first partition 132-1 may include a first plate 1321, a second plate 1322, and a plate connection portion 1323.

The first plate 1321 may be secured to the first cabinet (11 of FIG. 13). More specifically, the first plate 1321 may be secured to the first cabinet (11 of FIG. 13) at a rear portion of the first inner space IS1 defined by the first cabinet (11 of FIG. 13).

The second plate 1322 may be connected to the first plate 1321 through the plate connection portion 1323. When the 2nd first partition is in the unfolded position, the second plate 1322 may be located in front of the first plate 1321.

The plate connection portion 1323 may be pivotally coupled to each of the first plate 1321 and the second plate 1322.

FIG. 8 is a sectional view of the 2nd first partition 132-1 of the shoe management apparatus according to the embodiment of the present disclosure, wherein the 2nd first partition is in the unfolded position. FIG. 9 is an enlarged view of section 132A of FIG. 8.

The first plate 1321 may be formed therein with a first plate fluid path AP1, and the second plate 1322 may be formed therein with a second plate fluid path AP2. In addition, the second plate 1322 may be formed on a lower surface thereof with a second plate exhaust port 13224 through which air is discharged, the second plate exhaust port 13224 may be provided in plurality and may extend longitudinally across the second plate 1322.

The plate connection portion 1323 may be pivotally connected to both a front upper portion of the first plate 1321 and a rear upper portion of the second plate 1322. Accordingly, the front upper portion of the first plate 1321 is secured to the rear upper portion of the second plate 1322 through the plate connection portion 1323. In this state, a rear lower portion of the second plate 1322 is supported by a front lower portion of the first plate 1321, whereby an upper surface of the second plate 1322 and an upper surface of the first plate 1321 can remain connected to each other to form a continuous plane.

When the 2nd first partition 132-1 is in the unfolded position, the first plate fluid path AP1 formed in the first plate 1321 may be connected to the second plate fluid path AP2 formed in the second plate 1322. Accordingly, when the 2nd first partition 132-1 is in the unfolded position, air discharged from the electric compartment (20 of FIG. 3) can be delivered to the second plate exhaust port 13224 through the first plate fluid path AP1 and the second plate fluid path AP2. That is, when the 2nd first partition 132-1 is in the unfolded position, air can be discharged in a downward direction from the front region of the first inner space IP1 through the 2nd first partition 132-1.

Each of the first plate fluid path AP1 and the second plate fluid path AP2 has a larger cross-sectional area at a point at which the first plate fluid path AP1 and the second plate fluid path AP2 meet each other when the 2nd first partition 132-1 is in the unfolded position than at the other points. That is, the first plate fluid path AP1 has the largest cross-sectional area at a front end thereof and the second plate fluid path AP2 has the largest cross-sectional area at a rear end thereof. With this structure, it is possible to provide a smooth flow of air from the first plate fluid path AP1 to the second plate fluid path AP2 when the 2nd first partition 132-1 is in the unfolded position.

FIG. 10 is a perspective view of the 2nd first partition 132-1 of the shoe management apparatus according to the embodiment of the present disclosure, wherein the 2nd first partition is in a folded position, and FIG. 11 is a sectional view of the 2nd first partition 132-1 of the shoe management apparatus according to the embodiment of the present disclosure, wherein the 2nd first partition is in the folded position.

As described above, the plate connection portion 1323 may be pivotally connected to the front upper portion of the first plate 1321 and the rear upper portion of the second plate 1322. Accordingly, the second plate 1322 may be pivoted upwards about the plate connection portion 1323. When the 2nd first partition 132-1 is in the folded position, the second plate 1322 may be located on the upper surface of the first plate 1321. The first plate 1321 may be formed on a front surface thereof with a first plate exhaust port 13214 through which air is discharged.

When the 2nd first partition 132-1 is in the folded position, air discharged from the electric compartment (20 of FIG. 3) is delivered to the first plate exhaust port 13214 through the first plate fluid path AP1. That is, when the 2nd first partition 132-1 is in the folded position, air can be discharged through the first plate 132-1 in a forward direction from the middle region of the first inner space IS1 with respect to the front-to-rear direction. In addition, as described above, the first plate fluid path AP1 may be increased in cross-sectional area toward the first plate exhaust port 13214. In this way, the air discharged from the first plate exhaust port 13214 can be more widely diffused.

The 3rd first partition 133-1 may have the same structure as the 2nd first partition 132-1 shown in FIG. 7 to FIG. 11.

FIG. 12 shows a case in which a boot is placed in the first management apparatus 10 of the shoe management apparatus 1 according to the embodiment of the present disclosure, and FIG. 13 shows a case in which a sneaker is placed in the first management apparatus 10 of the shoe management apparatus 1 according to the embodiment of the present disclosure.

For the boot placed in the first inner space IS1 of the first management apparatus 10, the 2nd first partition 132-1 is folded such that air can be discharged therethrough (i.e., through the first plate exhaust port 13214) in a forward direction from the middle region of the first inner space IS1 with respect to the front-to-rear direction. In this way, it is possible to remove contaminants from a shaft of the boot and, if necessary, to coat the shaft.

For the sneaker placed in the first inner space IS1 of the first management apparatus 10, the 2nd first partition 132-1 is unfolded such that air can be discharged therethrough (i.e., through the second plate exhaust port 13224) in a downward direction from the front region of the first inner space IS1. In this way, it is possible to more effectively remove dust, sweat, and the like from inside the sneaker.

In addition, according to an embodiment of the present disclosure, the amount of air discharged through the 2nd first partition 132-1 can be increased due to operation of the first blower fan 171.

Further, the first blower fan 171 and the first inner panel 161 may allow air to flow in an obliquely downward direction from the rear of the first inner space IS1. That is, the first inner panel 161 may be positioned at an oblique angle with respect to the shoe to force air to be discharged at an oblique angle, and the air can be directed to a toe cap of the boot through the first inner panel 161. Thus, the shoe management apparatus according to the embodiment of the present disclosure can more efficiently perform an operation of removing contaminants from the shaft and toe cap of the boot or coating the shaft and toe cap of the boot.

Thus, the shoe management apparatus according to the present disclosure can more efficiently manage various types of shoes.

Although some exemplary embodiments have been described herein, it should be understood by those skilled in the art that these embodiments are given by way of example only, and that various modifications, variations, and alterations can be made without departing from the spirit and scope of the present disclosure. In addition, although advantageous effects provided by a certain configuration are not clearly described in description of the exemplary embodiments, it should be noted that expectable effects of the corresponding configuration should be acknowledged.

What is claimed is:

1. A shoe management apparatus, comprising:
a cabinet including an inner space for storing shoes;
a partition disposed in the inner space and configured to:
discharge air, in a first position, through the partition in a downward direction, and
discharge air, in a second position, through the partition in a forward direction; and
an inner panel disposed under the partition,
wherein the partition includes a first exhaust port for discharging air toward a shaft of one of the shoes, and
wherein the inner panel includes a second exhaust port disposed below the first exhaust port, the second exhaust port for discharging air toward a toe cap of the one shoe.

2. The shoe management apparatus according to claim 1, wherein the partition further includes:
a first plate coupled to the cabinet at a rear portion of the inner space and including on a front surface thereof a first plate exhaust port through which air is discharged;
a plate connection part pivotally coupled to the first plate; and
a second plate pivotally coupled to the plate connection part and including on a lower surface thereof a second plate exhaust port through which air is discharged.

3. The shoe management apparatus according to claim 2, wherein the plate connection part is pivotally coupled to a front upper portion of the first plate, and
wherein the plate connection part is pivotally coupled to a rear upper portion of the second plate.

4. The shoe management apparatus according to claim 2, wherein in the first position of the partition, the second plate is located in front of the first plate and,
wherein in the second position of the partition, the second plate is located on an upper surface of the first plate.

5. The shoe management apparatus according to claim 1, further comprising:
the inner panel disposed under the partition within the inner space and disposed at least partially at an angle with respect to a rear surface of the cabinet; and
a blower fan disposed between the inner panel and the rear surface of the cabinet and configured to force air into a plate fluid path of the partition along which air is discharged into the inner space.

6. The shoe management apparatus according to claim 5, wherein the inner panel is formed with an inner panel exhaust port through which air is discharged in an obliquely downward direction.

7. The shoe management apparatus according to claim 1, further comprising an electric compartment disposed under the inner space and configured to discharge air into the inner space.

8. A shoe management apparatus, comprising:
a cabinet including an inner space for storing shoes;
a partition dividing the inner space into a first compartment and a second compartment, the partition being variable in length with respect to a front-to-rear direction of the shoe management apparatus and including a plate fluid path along which air is discharged into the inner space; and
an inner panel disposed under the partition,
wherein the partition includes a first exhaust port for discharging air toward a shaft of one of the shoes, and
wherein the inner panel includes a second exhaust port disposed below the first exhaust port, the second exhaust port for discharging air toward a toe cap of the one shoe.

9. The shoe management apparatus according to claim 8, wherein the partition is configured to be movable between a first position in which the partition is fully extended and a second position in which the partition is folded,
wherein in the first position, the partition is configured to discharge air in a downward direction, and
wherein in the second position, the partition is configured to discharge air in a forward direction, the forward direction being substantially perpendicular to the downward direction.

10. The shoe management apparatus according to claim 9, wherein the partition further includes:
a first plate coupled to the cabinet at a rear portion of the inner space and including on a front surface a first plate exhaust port through which air is discharged in the second position of the partition;
a plate connection part pivotally coupled to the first plate; and
a second plate pivotally coupled to the plate connection part and including on a lower surface a second plate exhaust port through which air is discharged in the first position of the partition.

11. The shoe management apparatus according to claim 10, wherein the plate connection part is pivotally coupled to a front upper portion of the first plate, and
wherein the plate connection part is pivotally coupled to a rear upper portion of the second plate.

12. The shoe management apparatus according to claim 10, wherein in the first position of the partition, the second plate is located in front of the first plate, and
wherein in the second position of the partition, the second plate is located above the first plate.

13. The shoe management apparatus according to claim 8, further comprising:
the inner panel disposed under the partition within the inner space and disposed at least partially at an angle with respect to a rear surface of the cabinet; and
a blower fan disposed between the inner panel and the rear surface of the cabinet and configured to force air into the plate fluid path of the partition.

14. The shoe management apparatus according to claim 13, wherein the inner panel is formed with an inner panel exhaust port through which air is discharged in an obliquely downward direction.

15. The shoe management apparatus according to claim 8, further comprising an electric compartment disposed under the inner space and configured to discharge air into the inner space.

16. A shoe management apparatus, comprising:
a cabinet including an inner space for storing shoes;
a partition configured to be movable between a first position in which the partition is fully extended and a second position in which the partition is folded, the partition including:
a first plate coupled to the cabinet at a rear portion of the inner space and including on a front surface a first plate exhaust port through which air is discharged in the second position of the partition;
a plate connection part pivotally coupled to the first plate; and a second plate pivotally coupled to the plate connection part and including on a lower surface a second plate exhaust port through which air is discharged in the first position of the partition; and an inner panel disposed under the partition, wherein the partition further includes a first exhaust port for discharging air toward a shaft of one of the shoes, and wherein the inner panel includes a second exhaust port disposed below the first exhaust port, the second exhaust port for discharging air toward a toe cap of the one shoe.

17. The shoe management apparatus according to claim 16, wherein in the first position of the partition, the second plate is located in front of the first plate, and wherein in the second position of the partition, the second plate is located above the first plate.

18. The shoe management apparatus according to claim 16, further comprising:

the inner panel disposed under the partition within the inner space and disposed at least partially at an angle with respect to a rear surface of the cabinet; and a blower fan disposed between the inner panel and the rear surface of the cabinet and configured to force air into a plate fluid path of the partition along which air is discharged into the inner space.

19. The shoe management apparatus according to claim 18, wherein the inner panel is formed with an inner panel exhaust port through which air is discharged in an obliquely downward direction.

20. The shoe management apparatus according to claim 16, further comprising an electric compartment disposed under the inner space and configured to discharge air into the inner space.

* * * * *